United States Patent [19]

Scanlon

[11] Patent Number: 5,684,460

[45] Date of Patent: Nov. 4, 1997

[54] MOTION AND SOUND MONITOR AND STIMULATOR

[75] Inventor: Michael V. Scanlon, Silver Spring, Md.

[73] Assignee: The United States of America as represented by the Secretary of the Army, Washington, D.C.

[21] Appl. No.: 638,721

[22] Filed: May 9, 1996

Related U.S. Application Data

[63] Continuation of Ser. No. 292,441, Aug. 17, 1994, abandoned, and a continuation-in-part of Ser. No. 231,081, Apr. 22, 1994, Pat. No. 5,515,865.

[51] Int. Cl.$^6$ .................................................. G08B 21/00
[52] U.S. Cl. ............................................ 340/573; 128/721
[58] Field of Search ............................. 340/573; 128/721

[56] References Cited

U.S. PATENT DOCUMENTS

| Re. 32,180 | 6/1986 | Lewiner et al. | 340/573 |
|---|---|---|---|
| 3,547,106 | 12/1970 | Bommann | 340/573 |
| 3,972,320 | 8/1976 | Kalman | 340/573 |
| 4,146,885 | 3/1979 | Lawson, Jr. | 340/573 |
| 4,438,771 | 3/1984 | Friesen et al. | 340/573 |
| 4,619,270 | 10/1986 | Margolis et al. | 128/721 |
| 4,630,614 | 12/1986 | Atlas | 128/721 |
| 4,694,839 | 9/1987 | Timme | 128/721 |
| 4,813,427 | 3/1989 | Schlaefke et al. | 128/671 |
| 4,862,144 | 8/1989 | Tao | 340/573 |

OTHER PUBLICATIONS

Gundersen and Dahlin, "Monitoring Of Breathing with a Segmental Air–Filled Mattress", *Med. & Biol. Engng.*, vol. 9, pp. 541–547, Sep. 1971.

*Primary Examiner*—Glen Swann
*Attorney, Agent, or Firm*—Freda L. Krosnick; Willaim E. Eshelman; Charles H. Harris

[57] ABSTRACT

A movement monitor and stimulator may prevent death in human infants from sudden infant death syndrome (SIDS). Recent medical studies indicate a SIDS victim's breathing may be resuscitated by immediate stimulation. The sound and/or movement monitor and stimulator may have a base member configured as a fluid-filled sensing pad for supporting an infant and a transducer for detecting movement or acoustic activity (e.g., heart beat, breathing, voice and motion sounds). A stimulator may move the base member to stimulate movement in the object when output from the transducer corresponds to no sound and/or movement from the object, or indicates a dangerous change in monitored condition, such as the decrease in metabolic rate indicative of the onset of sleep. The stimulator may also be applied in a more gentle fashion to soothe and quiet an infant that has been awakened unexpectedly. The transducer may be a pressure transducer in fluid communication with the fluid interior of the sensing pad. Alternatively, a piezoelectric sheet operatively connected to a surface of the sensing pad may detect movement and movement cessation. An alarm may provide an audible and/or visual indication to third parties when there is no movement from the object. A transmitter may continuously transmit the sensor's output to a remote location for monitoring. A remote monitor may transmit heart and breathing sounds and may also have lights indicating motion and acoustic activity to indicate the infant is breathing.

14 Claims, 3 Drawing Sheets

MOTION AND SOUND MONITOR AND STIMULATOR

This is a continuation of patent application Ser. No. 08/292,441, filed Aug. 17, 1994, now abandoned, and a continuation-in-part of patent application Ser. No. 08/231,081 filed Apr. 22, 1994, and issued May 14, 1996, as U.S. Pat. No. 5,515,815.

TECHNICAL FIELD

The present invention relates to a sound and movement monitor suitable for detecting activity and, more particularly, to a sound and movement monitor suitable for monitoring and stimulating/resuscitating a human or other living organism's breathing movement.

BACKGROUND ART

Apnea is a condition where a child or adult stops breathing temporarily, until something startles them into breathing again. Either an external stimulus, such as a noise or being shaken, or some internal reflex acts to restore regular breathing. Apnea, of any duration, limits the amount of oxygen supplied to the brain, and can damage brain cells and interfere with sleep.

Sudden Infant Death Syndrome (SIDS) is a different type of medical condition whereby an infant suddenly stops breathing, leading to the eventual death of the infant. Although the cause and initial symptoms of SIDS is not completely understood, it is felt that a child can be awakened from the SIDS condition if stimulated immediately.

Unfortunately, many currently available baby monitors are usually only provided with a microphone/transmitter and a receiver/speaker, enabling the parents to monitor airborne baby noises such as crying, coughing, sneezing and sniffling. If the parents do not hear anything, they assume the baby is sleeping, and therefore do not need to check in on the child. Unfortunately, in some tragic situations, the absence of baby noises can be deadly to the child.

Consequently, other devices are known in the art which monitor breathing or baby motion to sound an alarm in the absence of such breathing or motion. U.S. Pat. No. 4,438,771, for example, discloses an apparatus for detecting the cessation of body movement by detecting the voltage produced by the movement of the charge on the body attributable to such movement. This is accomplished by a passive contactless conductive pad which is spaced from the body and in which a potential is induced by the movement of the body through the movement of the charge on the body. This potential is amplified and an alarm indication device responds to the amplified potential to produce an alarm when the output of the amplifier is below a predetermined value for a predetermined period of time. With this device, an alarm indication is provided to the parents which then necessitates a proactive role by the parents to start the artificial respiratory procedures necessary to induce continued rhythmic breathing.

Another movement monitor is disclosed in U.S. Pat. No. 4,862,144 wherein the apparatus disclosed therein monitors motion and breathing by transmitting pressure signals to a pad by means of a strap secured around the person's body to facilitate forced transmission. The present or absence of breathing motion is monitored and logic circuitry can be actuated to provide an alarm should the output from the transducer sense no movement from the moving object. Again, however, the alarm necessitates a proactive role on the part of parents or third parties to try to stimulate breathing of the child upon receipt of the alarm.

SUMMARY OF THE INVENTION

It is accordingly one object of the present invention to detect the absence of breathing, heartsounds, movement of a living organism and then attempt to stimulate breathing movement with at least some type of physical movement or sound applied to the organism.

Another object is to monitor for the absence of breathing by the use of passive sensors, and preferably without any restraint devices and without impeding normal movement of the organism.

Yet another object is to provide a movement monitor and stimulator suitable for use with adults or other respiring animals.

Still a further object is to stimulate movement of a living organism upon breathing or heartbeat cessation while optionally providing an alarm to alert and solicit professional or parental assistance in the performance of further lifesaving procedures subsequent to the initial physical stimulus measures provided prior to response to the alarm.

A sound or movement monitor and stimulator, in accordance with the present invention, comprises a base member for supporting an object in which movement is being monitored, and a transducer positioned for detecting acoustic activity or movement of the object on the base member. The transducer provides an output signal in response to forces applied thereto which are generated by and representative of said activity or movement. A circuit is connected to monitor the output signal from the transducer. A stimulator is connected to the circuit and is operable to provide at least physical movement to the base member or directly to the object to stimulate movement in the object when the transducer output to the circuit corresponds to no sound and/or movement (below a predetermined threshold) or, optionally, abnormal activity from the object.

The "transducer," as used in this specification, may be a microphone or similar means for picking up acoustic signals (e.g., heartbeat) and/or varying pressure signals. The transducer could also be a vibratory and/or movement sensor, such as accelerometer, strain gage, optical displacement sensor, or fiber-optic. Chemical, biological, and electrical emission sensors could also be used as a transducer to indicate the condition of the object.

The transducer output, in accordance with the preferred embodiment, can be transmitted to a remote location and monitored by audio and visual indicators of sensor activity. Respiratory, pulmonary, digestive, and vocalized sounds transduced can be recreated at the remote monitor, or transmitted to medical personnel for diagnosis and treatment. A remote station could be configured to monitor one or more sensor pads simultaneously, and selectively choose to monitor each of the transducer's audio output.

Preferably, in the preferred embodiment, the stimulator generates vibratory, oscillatory or shaking movement of the base member and/or fluid within the pad in horizontal and/or vertical directions. The stimulator also preferably generates an audible noise to stimulate the object acoustically, and a light source to stimulate the object visually. Additionally, electrical, chemical, mechanical, or other energy sources could be used as a stimulator.

The base member, such as a sensor pad, preferably has characteristics sufficient to transmit to the transducer the movement from the object in the form of at least one of breathing, heart and motion sounds of the object. The shape and performance features of the pad will be tailored to each application, such as for use in a crib, cradle, vehicle seat, or stroller. The base member and transducer could also be built into existing products. In the preferred embodiment, the base member is a fluid-filled mattress and the transducer is a pressure transducer arranged in fluid communication with the internal fluid volume of the mattress such that forces applied to the mattress by the object cause pressure changes which are detected by the pressure transducer. The pressure transducer then provides an output proportional to the pressure changes. Preferably, the pressure transducer can also discriminate between the physical presence an absence of an object placed upon the sensor pad.

The mattress may be a sensor pad having top and bottom surfaces which are sufficiently rigid so as to facilitate transmission of pressure fluctuations from the object to the transducer. These surfaces should allow acoustic signals to be transmitted through the walls, facilitating communication between the object, fluid medium, and transducer.

In accordance with another embodiment of the invention, the transducer and the base member include a piezo-electric sheet which is operable to create a charge output when stressed or deformed by movement of the object and which is connected to the circuit to supply a voltage thereto to generate the output signal.

In accordance with another feature of the invention, the piezo-electric sheet may be operably positioned adjacent a sensor pad containing both a fluid and top and bottom surfaces which have characteristics sufficient for transmitting movement of the object to the piezo-electric sheet.

The invention may further comprise an alarm which is activated by the circuit when the output from the transducer corresponds to no movement (and/or absence of cardiopulmonary sounds) from the object. The alarm could also be activated upon indication of the onset of measurable symptoms indicative of certain conditions, such as falling asleep, snoring, or choking.

The movement stimulator preferably includes means for shaking the base member to stimulate movement of the object. Such shaking means may comprise a piston and cylinder arrangement, electro-magnetic, pneumatic, hydraulic, or piezo-electric actuators, a solenoid, or an eccentric (motor with an unbalanced mass on its shaft).

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BEST MODE FOR CARRYING OUT THE INVENTION

Figure 1:
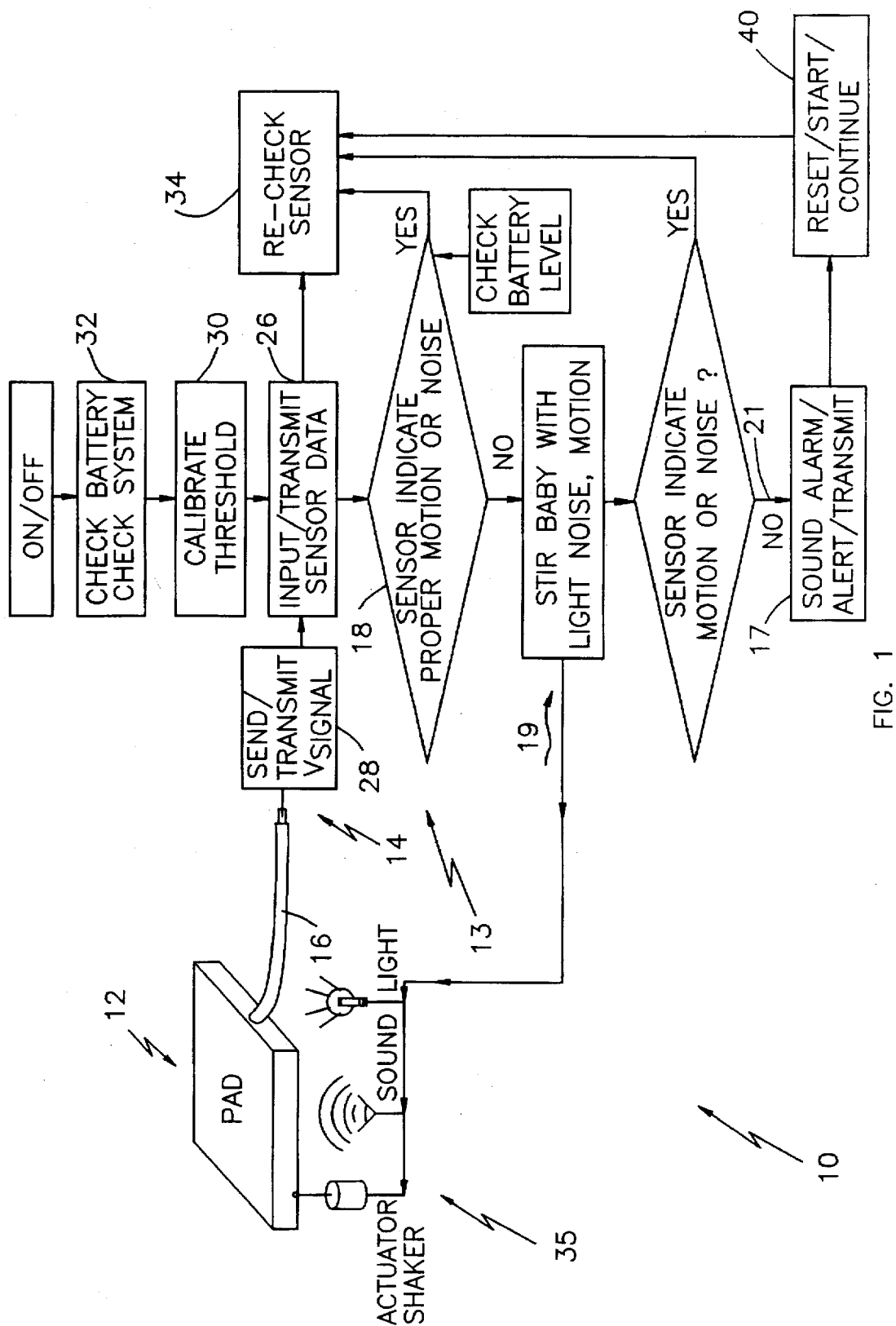
FIG. 1 is an illustration, partly in schematic form, of a presently preferred embodiment of a sudden infant death syndrome monitor and stimulator according to the present invention.

FIG. 1 is an illustration of a preferred embodiment of a sudden infant death syndrome monitor and stimulator, generally designated with reference numeral 10, wherein a sensor pad 12 placed beneath a child in a crib, incubator, bed or the like, is connected to a sensing and monitoring system 13 to monitor the pressure fluctuations of the fluid-filled pad such as may be caused by the child's breathing, heart and motion sounds. Since water is an excellent transmitter of sound, the preferred embodiment contemplates the use of a pressure transducer 14, connected to the water chamber in pad 12 through hose 16 or the like, which is provided to continuously sense the fluid for pressure fluctuations. However, the pressure sensor 14 can be located anywhere within fluid contact. The pressure transducer 14 may be a microphone, hydrophone, accelerometer, strain gage, a fluidic sensor, etc. The transduced output, presented in the form of audio and visual indicators, can be continuously monitored at the sensor pad location, and/or can be transmitted (e.g., via transmitter 50 in FIG. 3) to a remote location (receiver 52) for similar monitoring. Once the measured signal level has dropped below a pre-set threshold for a predetermined period of time (which may be medically and experimentally determined), indicating that the child or adult is not breathing, moving, not present, or that another dangerous condition exists, an alarm 17 may sound to alert professional or parental authorities. In accordance with the present invention, and independent from alarm actuation, monitor and system 10 uniquely features control circuitry and logic 18 used to actuate a stimulating means 19 and 35 connected either to pad 12 in order to shake or otherwise move the pad or the person directly to awaken or stimulate breathing.

Preferably, while monitoring the sensor 14 for signs of improvement, the system 10 would transmit or send an alert signal 21 for help. If the attempt to stir the baby was successful, the alert signal 21 may not be necessary, and the system 10 can be designed to continue to monitor the baby as usual without transmitting an alarm to parents or attendants.

Figure 2:
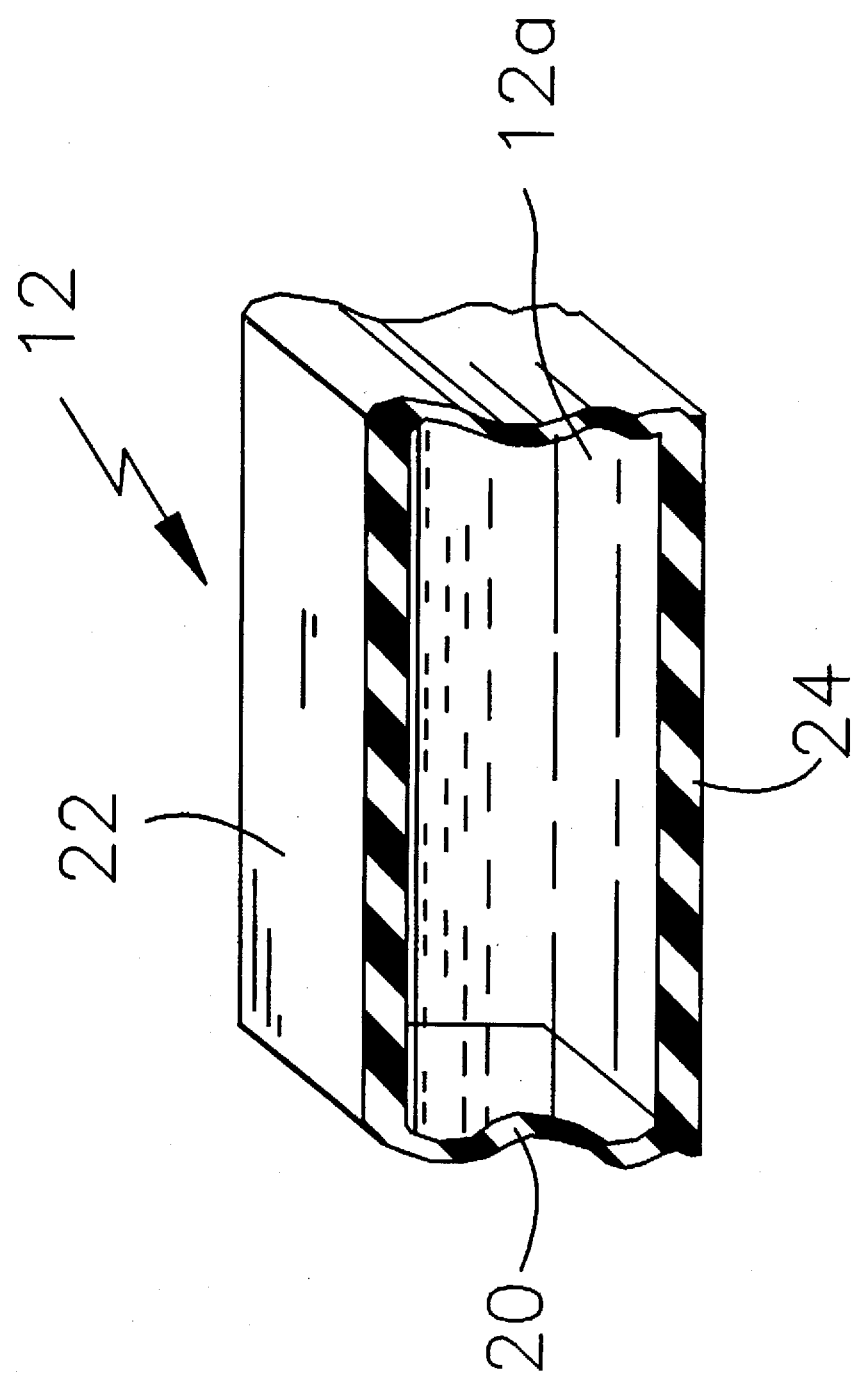
FIG. 2 is a detail sectional view of a exemplary sensor pad that may be used to practice the present invention.

The sensor pad 12, as best depicted in FIG. 2, is characterized by a mattress formed with an interior fluid chamber 12a (preferably containing water or air) having flexible side walls 20 and top and bottom walls 22 and 24 in a design which may be similar to a hot water bottle. These top and bottom walls 22,24 are preferably rigid or semi-rigid so as not to absorb pressure fluctuations. The rigidity of the walls 22,24 must facilitate acoustic transmission but are preferably not flexible enough to conform to the child's face and thereby restrict breathing.

The pad 12 may be formed with conduits (not shown in detail) within the pad interior 12a to ensure that pressure fluctuations are transmitted efficiently to the pressure transducer sensing element 14 which fluidly communicate with the pad interior or the conduits through hose 16 as discussed above.

An exemplary pad, hose and pressure transducer arrangement which may be used to practice the present invention is depicted in FIG. 5 of U.S. Pat. No. 4,862,144, issued Aug. 29, 1989, for a movement monitor. The above-mentioned Figure and related description in this '144 patent is hereby incorporated by reference herein.

In accordance with other embodiments that may be used to practice the present invention, the sensor pad 12 need not necessarily be fluid-filled. For example, piezo-electric sheet material (not shown in detail) can be used as the sensing element with or without the fluid-filled pad 12. Piezo-electric films create a charge output when stressed or deformed. When converted to a voltage, this charge output could be monitored in the same way as pressure transducer 14. A sheet or multiple strips of piezo-electric film material would be relatively inexpensive and would not produce an electromagnetic field or create a shock hazard since it does not have enough voltage applied to it. If used in combination with a fluid-filled pad 12, the fluid-filled pad may increase the performance of the piezo-electric film by allowing greater deformation of the film, as opposed to attachment of the piezo-electric film to top and/or bottom surfaces of a flexible, nonfluid-filled pad (not shown in detail).

The electronic circuitry 18,19,26 associated with system 10 is relatively simple and the selection and design of such circuitry will be obvious to an electrical engineer of ordinary skill upon review of this specification. Briefly, a voltage comparator 26 constantly monitors the output signal 28 from pressure transducer 14. Transmitter 50 can also continuously transmit this signal for remote listening and monitoring. If signal 28 falls below a certain threshold level (calibrated at step 30), appropriate timing and alarm circuits 18,19 which may operate a gating logic circuit are used to activate the visual and/or audible alarm 17. The various circuit means, preferably battery operated as at 32, may be identical or similar to the disclosed circuitry means in FIGS. 9 and 11 of the aforesaid U.S. Pat. No. 4,862,144, such figures and relevant figure descriptions therein being incorporated by reference herein. Other types of voltage comparator circuits, level detectors, and change-in-state circuits as well known in the art may also be utilized. Additional components such as filters or digital signal processors as known in the art may be used to remove unnecessary noise and enhance or identify the signals of interest in step 18.

Once the danger condition (such as the decrease in cardiovascular and/or metabolic rate, absence of breathing, heart movement, etc.) is detected, the circuitry means of this invention is also advantageously connected to a noise or vibrator or other means, generally designated by reference numeral 35 in FIG. 1, to apply a stimulus to the pad 12. Preferably, any stimulus applied to the object and/or pad 12 includes at least active shaking or other type of movement applied to the pad so as to physically move the child to reactivate breathing.

After the stimulus has been applied for a predetermined length of time as determined by the timing circuit, the circuit may re-set as at 34 to the normal monitoring condition to evaluate whether the stimulus is effective. If not effective, the stimulus may be re-applied and the alert sounded or re-sounded. With the use of a transmitter, parents/doctors could also check the signal being generated.

The system 10 may also feature a sensor sensitivity adjustment or an alarm threshold adjustment which would calibrate the system to its environment. Adjusting the threshold of the system 10 to respond to the "baby not present" condition, would calibrate the device to not respond when the baby is placed on the sensor pad 12. When the baby is present and breathing on the pad 12, the output level would be higher than room noise. If this level drops to room noise for a predetermined length of time, the system 10 would either sound an alarm or attempt to stir the baby. If the baby is successfully stirred, the alarm is re-set and continues to monitor.

As mentioned above, the sensor 14 in the fluid-filled system may be a piezo-electric or ceramic hydrophone, similar to those used by the U.S. Navy in active and passive sonar applications. The synergistic combination of different sensor technologies placed inside, on, or near the sensor pad 12 can enhance reliability of system performance. Using multiple sensors in an array configuration can also improve signal to noise ratio (SNR) and create focussed zones of sensing. Other one or more sensor technologies may also be used as will occur to one of ordinary skill. When installed at the edge of the fluid pad 12, or in a fluid-filled tube 16 extending from the pad and terminating in a diaphragm which transmits pressure to the sensor, the sensor would generate a voltage output corresponding to any pressure fluctuations within the fluid. These pressure fluctuations may be transmitted to conduits within the pad to ensure that such fluctuations are transmitted efficiently to the sensing element. Motion of the baby's torso during breathing will be transmitted to the fluid through the walls 22 and/or 24 and detected by the sensor 14. It is also possible to detect, as verified through experimentation, heartbeat, breathing, crying, and motion through the water pad. Such heartbeat and breathing sounds, in addition to motion noises, can be clearly detected with a microphone and tend to be significantly higher in amplitude than ambient noise.

Once the danger condition has been sensed for the proper duration as determined by the timing circuit, an attempt to stir the baby must be made immediately. As mentioned above, such a stimulus could be created by a loud acoustic source, such as a beeper, siren, solenoid, or bell. Preferably, however, a vibrating or other type of movement generating source 35 is used to transmit vibration and movement through the fluid pad 12 or directly to the frame of the bed or cradle in order to shake and restore breathing or wake the baby. Bright light may also assist in waking the baby. Parents or doctors can be notified through common methods, such as audio alarms, flashing lights, beepers or other transmitter devices as mentioned above. Immediate action by those present can significantly improve treatment.

The system 10 also features a low battery indicator 32 (e.g., light or sound), and system performance test button 40. As mentioned above, a sensor sensitivity adjustment or an alarm threshold adjustment is used to calibrate the system to its environment. An auto-calibration method could be incorporated to eliminate the need for adjustments.

The unique system 10 in accordance with the present invention has the potential to save the lives of many infants that are afflicted with sudden infant death syndrome (SIDS). Parents and medical staff will be able to relax somewhat in the knowledge that the baby is being constantly monitored for normal cardiopulmonary function.

It will now occur to one of ordinary skill in the art from reviewing this specification that, with slight modification, this invention may also be used for controlling general apnea, stop snoring, or sensing the onset of sleep for drivers of vehicles (e.g., by monitoring a slow down in heart rate and/or breathing). Machinery and other inanimate material can also be monitored for noises and vibrations indicative of atypical operation. An example would be a rotating system where imbalances might occur, and be corrected by providing stimulation in the form of vibrations to counteract or control the unwanted condition.

In accordance with another feature of this invention, it will now be appreciated by one of ordinary skill that the circuitry means 17 may also be used to transmit the data being monitored to parental or medical authorities and not merely provide a warning or alert indication. Data representative of breathing rate, for example, or perhaps heart sounds, may be transmitted and therefore monitored at a remote location.

Another unique feature of this invention which may be achieved through the vibrating means or shaker means connected to the pad 12 and operated by the circuitry means 19, is the ability to operate the shaker in a quieter, soothing amplitude mode to either assist the baby in falling asleep or to quiet the baby should it wake up unexpectedly. Pleasing and soothing audio, such as from a cassette player, can also be relayed to the child through the speaker used for audio stimulation, and the light indicators near the pad could provide soothing light patterns to occupy or distract the child. Appropriate circuitry modifications to the detection circuitry will be obvious to one of ordinary skill based upon this disclosure.

Upon detection of no movement or acoustic activity in the animate object, it is also possible to re-stimulate such movement or acoustic activity by means of electrical shock.

The circuitry employed in the preferred embodiment of this invention may also include outputs corresponding to heartbeat and breathing rates, as well as a clock for measuring elapsed time since a last warning, number of incidents, time of cessation of movement or acoustic activity, false alarms, etc.

A pressure switch can be used to turn the system off when the baby is removed from pad 12 to prevent alarms from going off without necessarily requiring the parents to turn the system off manually before removing the child. However, this feature may not be desirable if the pad is being used as a security device.

Figure 3:
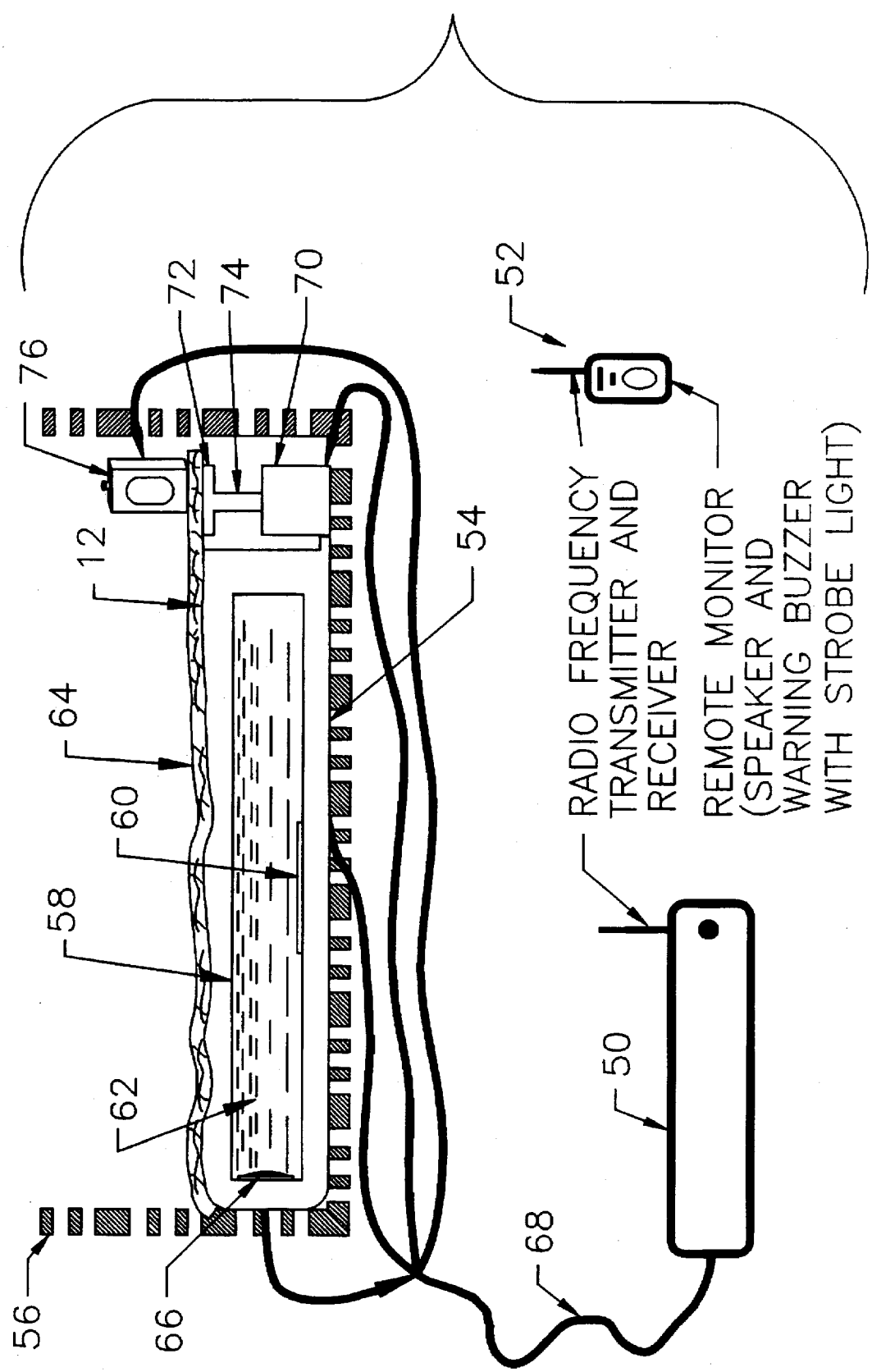
FIG. 3 is an illustration, partly in section and partly schematic, depicting variations and modifications within the preferred embodiment.

It should be understood that "baby waterbeds" are now available as commercial products. Therefore, the sensor and shaker mechanisms as well as the alarms identified hereinabove may be an attachment to existing waterbeds or related products as noted above. For example, FIG. 3 is an illustration of pad 12 disposed on a bottom support 54 within a bassinet or crib 56. A hot water bottle 58 and/or a heating element 60 may be disposed in thermal contact with the mattress or pad 12 to maintain the water 62 therein at a desirable temperature. A blanket 64 covers the structure. A waterproof microphone 66 may be optionally disposed in fluidic contact with the water 62 in mattress 12 to monitor acoustic activity as aforesaid. The appropriate signals 28, as discussed in detail above, may be monitored on site and/or transmitted via cable 68 to a signal processor 50 for remote transmission to a remote receiver 52, also as discussed above.

Movement generating source 35 may be a solenoid 70 adapted to shake a rigid member 72 through solenoid plunger 74 to create the aforesaid physical movement in an attempt to awaken the person. This movement may be assisted by means of a buzzer alarm (with or without a warning light) 76.

Different color light indicators on the sensor pad and remote monitor can indicate the occurrence of heartbeats, breathing, and motion sounds. Indicators for adequate power, proper system function, and within effective transmit/receive range can be incorporated.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. A sound and movement monitor and stimulator, comprising:

(a) a fluid-filled mattress for supporting an animate object;

(b) a sound and movement transducer positioned for detecting movement activity and acoustic activity of the object on said mattress, said transducer providing an output signal in response to forces applied thereto which are generated by and representative of said activity, said transducer including a pressure transducing element arranged in fluid communication with the internal fluid volume of said mattress such that forces applied to said mattress by said object cause pressure changes which are detected by said pressure transducing element, said pressure transducing element providing an output proportional to the pressure changes;

(c) a circuit connected to said transducer and adapted to monitor said output signal from said transducer; and (d) a stimulator connected to said circuit and being operable to provide at least physical movement to the object to stimulate movement or acoustic activity in the object when the output from said transducer to said circuit corresponds to no movement activity and no acoustic activity from the object; wherein said mattress is configured so said activity from the object including at least one of breathing, heart and motion sounds of the object is transmitted to said transducer said mattress including top and bottom surfaces which are sufficiently rigid so as to facilitate transmission of pressure fluctuations from the object to said transducer.

2. The sound and movement monitor and stimulator of claim 1, wherein said stimulator generates vibratory movement of said mattress.

3. The sound and movement monitor and stimulator of claim 1, further comprising an alarm actuated by said circuit when said output from said transducer corresponds to at least one of no movement from the object and absence of predetermined acoustic signals.

4. The sound and movement monitor and stimulator of claim 1, wherein said stimulator includes means for shaking said mattress to stimulate movement of the animate object.

5. The sound and movement monitor and stimulator of claim 1, wherein said output signal from the transducer is transmitted to a remote location for monitoring.

6. The sound and movement monitor and stimulator of claim 1, wherein said stimulator generates at least one of sound, light, electrical, chemical, or mechanical stimulation to at least one of said mattress and the animate object.

7. The sound and movement monitor and stimulator of claim 1, wherein said mattress is a liquid-filled mattress, and said transducer includes a sound transducing element configured so sounds from the animate object are detected and converted to electrical signals for transmission to said circuit.

8. An acoustic monitoring system comprising:

a liquid-filled sensor pad adapted to support an animate object;

acoustic transducing means for monitoring and converting acoustic activity of the animate object on said sensor pad to electrical signals corresponding to the monitored acoustic activity;

a circuit connected to said acoustic transducing means and adapted to receive the electrical signals from said acoustic transducing means;

a transmitter located at a first position and connected to said circuit, said transmitter configured to transmit signals corresponding to the acoustic activity of the animate object;

a receiver located at a second position spaced apart from said first position and configured to receive signals from said transmitter; and a physical stimulator connected to said circuit and adapted to physically move said sensor pad and the animate object, when the electrical signals from said acoustic transducing means correspond to no acoustic activity of the animate object.

9. The acoustic monitoring system of claim 8, further comprising an alarm connected to said circuit, said alarm including a sound emitting element.

10. The acoustic monitoring system of claim 9, wherein said alarm further includes a light emitting element.

11. A method of monitoring and stimulating an animate object comprising the steps of:

determining acoustic activity of an animate object;

transmitting a first signal corresponding to the acoustic activity to a control element;

stimulating the animate object when the first signal received by the control element corresponds to no acoustic activity from the animate object.

12. The method according to claim 11, further comprising the steps of:

determining movement activity of an animate object;

transmitting a second signal corresponding to the movement activity to the control element;

stimulating the animate object when the second signal received by the control element corresponds to no movement activity from the animate object.

13. The method according to claim 12, further comprising the step of actuating an alarm when the signals received by the control element corresponds to at least one of no movement activity and no acoustic activity from the animate object.

14. The method according to claim 13, further comprising the step of transmitting the signals received by the control element to a location remote from the control element for monitoring by a user.

* * * * *